（12）United States Patent
Noda

(10) Patent No.: US 11,832,983 B2
(45) Date of Patent: Dec. 5, 2023

(54) INFORMATION PROCESSING APPARATUS AND METHOD, AND RADIOGRAPHY SYSTEM

(71) Applicant: CANON KABUSHIKI KAISHA, Tokyo (JP)

(72) Inventor: Takeshi Noda, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 393 days.

(21) Appl. No.: 17/237,842

(22) Filed: Apr. 22, 2021

(65) Prior Publication Data

US 2021/0236078 A1  Aug. 5, 2021

Related U.S. Application Data

(63) Continuation of application No. PCT/JP2019/038717, filed on Oct. 1, 2019.

(30) Foreign Application Priority Data

Nov. 9, 2018  (JP) .................................. 2018-211700

(51) Int. Cl.
*A61B 6/00* (2006.01)
*G06T 7/00* (2017.01)
*A61B 6/12* (2006.01)

(52) U.S. Cl.
CPC ................ *A61B 6/482* (2013.01); *A61B 6/12* (2013.01); *A61B 6/405* (2013.01); *A61B 6/4085* (2013.01);

(Continued)

(58) Field of Classification Search
CPC .. A61B 6/12; A61B 6/40; A61B 6/405; A61B 6/4085; A61B 6/42; A61B 6/4208;
(Continued)

(56) References Cited

U.S. PATENT DOCUMENTS 6,226,352 B1 * 5/2001 Salb ..................... A61B 6/4035
378/143
6,463,121 B1 * 10/2002 Milnes ................. A61B 6/4482
378/98.2

(Continued)

FOREIGN PATENT DOCUMENTS

CN  108181326 A  6/2018
EP  0 549 858 A2  7/1993
(Continued)

OTHER PUBLICATIONS

Pier Luca-Rossi, et al., Imaging Characterization of a Multi-Energy CT with Quasi-Monochromatic X-ray source, IEEE Nuc. Sci. Symp. Conf. Record (2011) 2832-35.

*Primary Examiner* — Allen C. Ho
(74) *Attorney, Agent, or Firm* — VENABLE LLP

(57) ABSTRACT

An image processing apparatus obtains at least three radiation images obtained based on radiation emitted onto an object, and corresponding to at least three types of energy, and separates a predetermined substance having a known attenuation coefficient in the object and a remaining substance other than the predetermined substance in the object, based on the at least three radiation images and calculating an effective atomic number of the remaining substance.

15 Claims, 4 Drawing Sheets

(52) U.S. Cl.
CPC .......... *A61B 6/4241* (2013.01); *A61B 6/4283* (2013.01); *A61B 6/463* (2013.01); *A61B 6/465* (2013.01); *A61B 6/481* (2013.01); *A61B 6/486* (2013.01); *A61B 6/487* (2013.01); *A61B 6/504* (2013.01); *A61B 6/5205* (2013.01); *A61B 6/5211* (2013.01); *A61B 6/5217* (2013.01); *G06T 7/0012* (2013.01); *G06T 2207/10116* (2013.01); *G06T 2207/30008* (2013.01); *G06T 2207/30096* (2013.01)

(58) Field of Classification Search
CPC ... A61B 6/4233; A61B 6/4241; A61B 6/4283; A61B 6/463; A61B 6/465; A61B 6/481; A61B 6/482; A61B 6/486; A61B 6/487; A61B 6/503; A61B 6/504; A61B 6/505; A61B 6/52; A61B 6/5205; A61B 6/5211; A61B 6/5217
USPC ...... 378/62, 98.9, 98.11, 189, 190, 196–198, 378/5, 42, 53–56; 382/130–132
See application file for complete search history.

(56) References Cited

U.S. PATENT DOCUMENTS

| | | | | |
|---|---|---|---|---|
| 7,158,611 B2 * | 1/2007 | Heismann | ............ | A61B 6/4035 378/53 |
| 7,366,282 B2 * | 4/2008 | Peschmann | ............ | G01N 23/04 378/57 |
| 7,564,943 B2 * | 7/2009 | Sommer, Jr. | .......... | B07C 5/3422 378/53 |
| 7,643,866 B2 * | 1/2010 | Heismann | .............. | A61B 6/504 600/458 |
| 7,809,103 B2 * | 10/2010 | Du | .......................... | G01N 23/10 378/53 |
| 7,983,390 B2 * | 7/2011 | Kitamura | ............. | A61B 6/4291 378/98.12 |
| 8,009,883 B2 * | 8/2011 | Ying | .................... | G01V 5/0008 382/128 |
| 8,355,594 B2 | 1/2013 | Noda et al. | | |
| 8,654,921 B2 | 2/2014 | Cho | | |
| 8,655,034 B2 | 2/2014 | Noda et al. | | |
| 8,744,210 B2 | 6/2014 | Noda et al. | | |
| 8,923,589 B2 | 12/2014 | Noda et al. | | |
| 8,942,347 B2 | 1/2015 | Cho | | |
| 9,014,450 B2 | 4/2015 | Noda et al. | | |
| 9,052,266 B2 * | 6/2015 | Miyazaki | ............. | G01N 23/046 |
| 9,204,847 B2 * | 12/2015 | Flohr | ......................... | G06T 5/50 |
| 9,274,037 B2 * | 3/2016 | Huwer | ................. | G01N 23/046 |
| 9,326,743 B2 * | 5/2016 | Shen | ...................... | A61B 6/482 |
| 9,532,759 B2 * | 1/2017 | Taguchi | .................. | A61B 6/032 |
| 9,820,713 B2 | 11/2017 | Noda et al. | | |
| 9,953,414 B2 | 4/2018 | Noda | | |
| 10,451,568 B2 * | 10/2019 | Moriyasu | ............... | G16H 50/20 |
| 10,713,784 B2 * | 7/2020 | Machida | ................ | A61B 6/585 |
| 11,016,040 B2 * | 5/2021 | Yamakawa | ........... | A61B 6/5282 |
| 11,058,384 B2 * | 7/2021 | Konno | .................... | A61B 6/482 |
| 11,112,528 B2 * | 9/2021 | Xu | ........................ | G01N 23/087 |
| 11,179,115 B2 * | 11/2021 | Konno | .................... | G06T 11/003 |
| 11,185,301 B2 * | 11/2021 | Torii | ...................... | A61B 6/482 |
| 11,207,041 B2 * | 12/2021 | Prabhu Verleker | ...... | A61B 6/52 |
| 11,298,095 B2 * | 4/2022 | Zhao | .................... | A61B 6/5235 |
| 11,331,068 B2 * | 5/2022 | Yamakawa | .......... | G01N 23/087 |
| 11,350,894 B2 * | 6/2022 | Machida | ................ | A61B 6/505 |
| 11,357,455 B2 * | 6/2022 | Noda | ..................... | A61B 6/503 |
| 11,360,034 B2 * | 6/2022 | Torii | ...................... | G01N 23/04 |
| 11,422,098 B2 * | 8/2022 | Iwashita | .................. | G01T 1/17 |
| 11,430,161 B2 * | 8/2022 | Iwashita | ................... | G06T 5/20 |
| 11,635,392 B2 * | 4/2023 | Noda | .................... | A61B 6/4233 378/62 |
| 2013/0101089 A1 | 4/2013 | Cho | | |
| 2018/0263576 A1 | 9/2018 | Konno | | |
| 2019/0320993 A1 | 10/2019 | Noda et al. | | |
| 2020/0163630 A1 | 5/2020 | Noda et al. | | |
| 2020/0309987 A1 | 10/2020 | Xu | | |
| 2021/0007691 A1 | 1/2021 | Prabhu | | |
| 2021/0055233 A1 | 2/2021 | Noda et al. | | |
| 2021/0118193 A1 | 4/2021 | Torii et al. | | |

FOREIGN PATENT DOCUMENTS

| | | |
|---|---|---|
| JP | H05-237081 A | 9/1993 |
| JP | H08-178873 A | 7/1996 |
| JP | 2008-142435 A | 6/2008 |
| JP | 2011-217805 A | 11/2011 |
| JP | 2016-145778 A | 8/2016 |
| JP | 2018-15664 A | 2/2018 |
| WO | 2017/073399 A1 | 5/2017 |

* cited by examiner

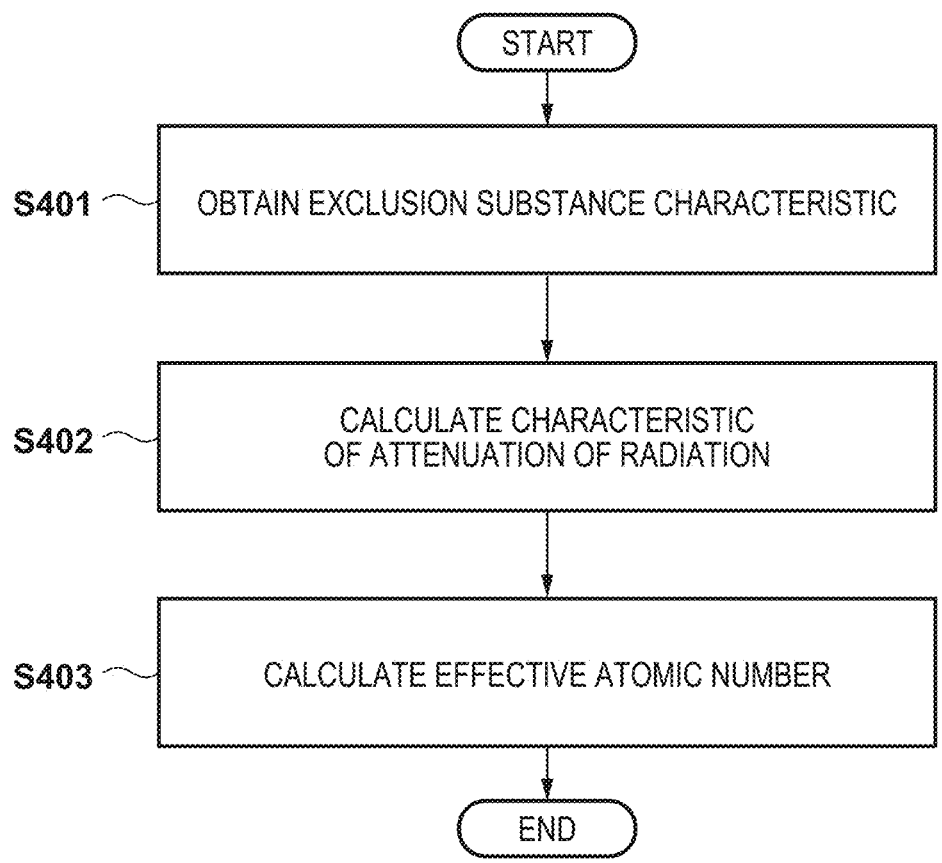

INFORMATION PROCESSING APPARATUS AND METHOD, AND RADIOGRAPHY SYSTEM

CROSS-REFERENCE TO RELATED APPLICATIONS

This application is a Continuation of International Patent Application No. PCT/JP2019/038717, filed Oct. 1, 2019, which claims the benefit of Japanese Patent Application No. 2018-211700, filed Nov. 9, 2018, both of which are hereby incorporated by reference herein in their entirety.

BACKGROUND OF THE INVENTION

Field of the Invention

The present invention relates to an information processing apparatus and method, and a radiography system.

Background Art

Radiation image capture apparatuses that use a flat panel detector (hereinafter, abbreviated as an "FPD") are in widespread use as shooting apparatuses that are used for medical image diagnosis performed using radiation. The FPD is capable of performing digital image processing of a shot image, and thus various applications have been developed and practically used.

Patent Document 1 discloses a method for emitting radiation of two energy values, and, regarding a measurement target made up of three substances that have different effective atomic numbers, determining the identities and the quantities of a plurality of substances. Also, Patent Document 2 discloses a method for emitting radiation of a plurality of energy values, and accurately obtaining an effective atomic number with a reduced error.

CITATION LIST

Patent Literature

PTL1: Japanese Patent Laid-Open No. 05-237081
PTL2: Japanese Patent Laid-Open No. 08-178873

When radiation passing through an object has passed through two or more types of substances, if the object includes a contrast agent and a soft substance such as fat in a human body, for example, the effective atomic number of the contrast agent is calculated as an effective atomic number subjected to averaging with the soft substance such as fat. In this case, in the method described in Patent Document 2, there may be cases where it is not possible to accurately calculate the effective atomic number of the contrast agent.

SUMMARY OF THE INVENTION

The present invention provides a technique that makes it possible to more accurately calculate an effective an atomic number in a radiation image.

According to one aspect of the present invention there is provided an information processing apparatus comprising: an obtaining unit configured to obtain at least three radiation images obtained based on radiation emitted onto an object, and corresponding to at least three types of energy; and a calculation unit configured to separate a predetermined substance having a known attenuation coefficient in the object and a remaining substance other than the predetermined substance in the object, based on the at least three radiation images and to calculate an effective atomic number of the remaining substance.

According to another aspect of the present invention there is provided a radiography system comprising: the information processing apparatus comprising: an obtaining unit configured to obtain at least three radiation images obtained based on radiation emitted onto an object, and corresponding to at least three types of energy; and a calculation unit configured to separate a predetermined substance having a known attenuation coefficient in the object and a remaining substance other than the predetermined substance in the object, based on the at least three radiation images and to calculate an effective atomic number of the remaining substance; and a radiation detection unit configured to detect the radiation and obtain the at least three radiation images.

According to another aspect of the present invention there is provided a radiography system comprising: an obtaining unit configured to obtain at least three types of energy information from a plurality of radiation images obtained based on radiation emitted onto an object; a first calculating unit configured to calculate a thickness or area density of a predetermined substance, based on at least three types of energy information; and a second calculating unit configured to calculate an effective atomic number for which the predetermined substance is excluded, based on the thickness or area density of the predetermined substance.

According to another aspect of the present invention there is provided an information processing method comprising: obtaining at least three radiation images obtained based on radiation emitted onto an object, and corresponding to at least three types of energy; and separating a predetermined substance having a known attenuation coefficient in the object and a remaining substance other than the predetermined substance in the object, based on the at least three radiation images and calculating an effective atomic number of the remaining substance.

According to another aspect of the present invention there is provided a non-transitory computer-readable storage medium storing a program for causing a computer to execute an information processing method comprising: obtaining at least three radiation images obtained based on radiation emitted onto an object, and corresponding to at least three types of energy; and separating a predetermined substance having a known attenuation coefficient in the object and a remaining substance other than the predetermined substance in the object, based on the at least three radiation images and calculating an effective atomic number of the remaining substance.

Further features of the present invention will become apparent from the following description of exemplary embodiments with reference to the attached drawings.

BRIEF DESCRIPTION OF THE DRAWINGS

FIG. 4 is a flowchart showing processing that is performed by an image processing unit according to a second embodiment.

DESCRIPTION OF EMBODIMENTS

Embodiments of the present invention will be described below exemplarily in detail with reference to the accompanying drawings. Note that constituent elements described in the following embodiments are merely exemplarily, and the technical scope of the present invention is determined by the claims, and is not limited by the individual embodiments below.

First Embodiment

Figure 1:
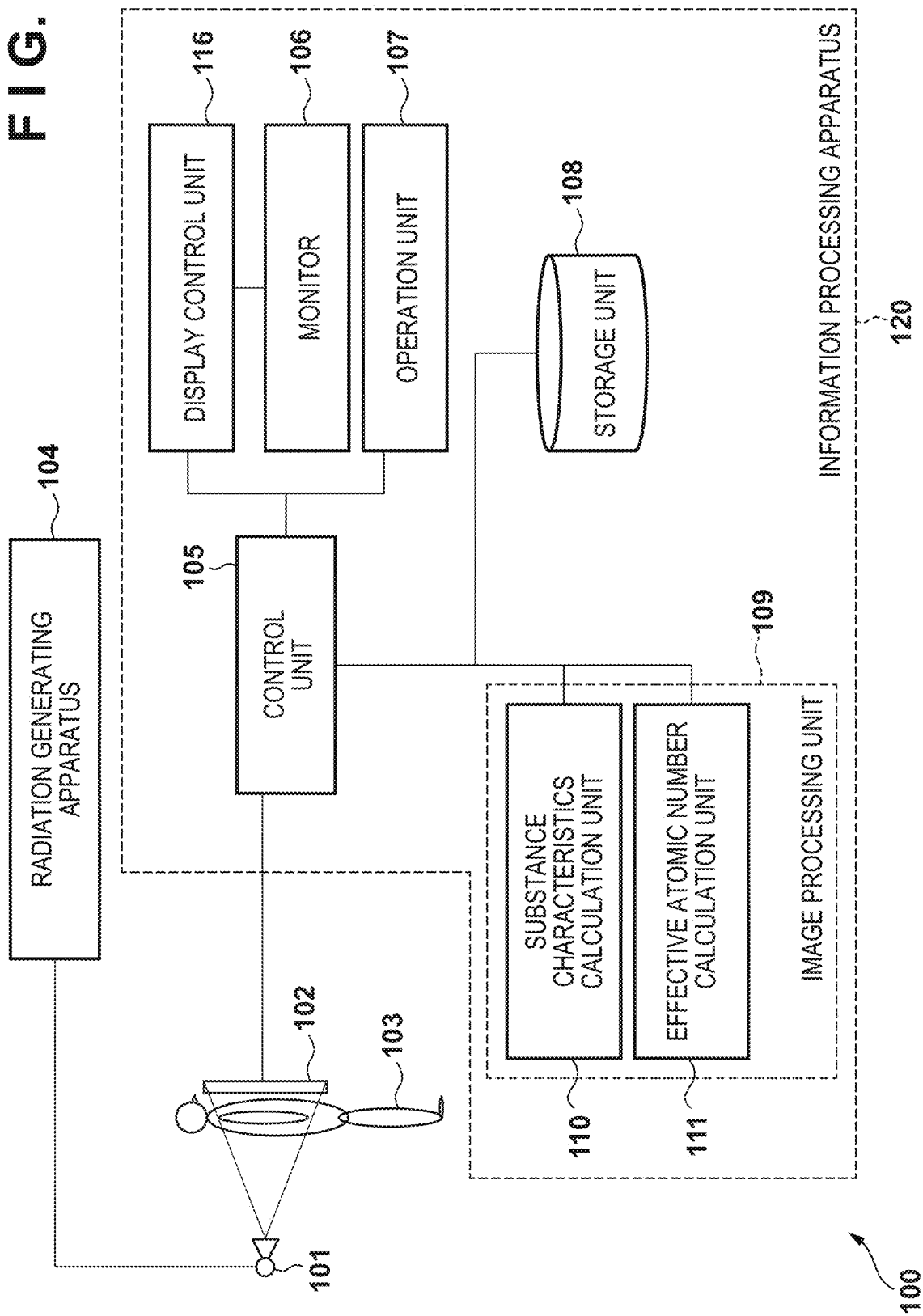
FIG. 1 is a diagram showing a configuration example of a radiography system according to a first embodiment.

FIG. 1 is a block diagram showing a configuration example of a radiography system 100 according to a first embodiment. The radiography system 100 includes a radiation generating apparatus 104, a radiation tube 101, an FPD 102, and an information processing apparatus 120. Note that the configuration of the radiography system 100 is simply referred to as a "radiography apparatus".

The radiation generating apparatus 104 applies high-voltage pulses to the radiation tube 101 in accordance with a user operation (for example, a pressing operation) performed on an exposure switch (not illustrated), and generates radiation. Note that the term "radiation" may include α-rays, β-rays, γ-rays, particle rays, cosmic rays, and the like in addition to X-rays. In an embodiment of the present invention, the type of radiation is not particularly limited, but X-rays are mainly used for medical image diagnosis. An object 103 is irradiated with radiation generated in the radiation tube 101, and a portion of the radiation passes through the object 103 and reaches the FPD 102.

Electric charges that are based on image signals accumulate in the FPD 102, which obtains a radiation image, and transfers the radiation image to the information processing apparatus 120. The FPD 102 includes a radiation detection unit (not illustrated) provided with a pixel array for generating signals that are based on radiation. The radiation detection unit detects, as image signals, radiation that has passed through the object 103. Pixels that output signals that are based on incident light are arranged in an array (two-dimensional region) in the radiation detection unit. Photoelectric conversion elements of the respective pixels convert visible light converted from radiation using a fluorescent body, into electrical signals, and output the signals as image signals. In this manner, the radiation detection unit is configured to detect radiation that has passed through the object 103, and obtain image signals (radiation image). A drive unit (not illustrated) of the FPD 102 outputs, to the control unit 105, image signals (radiation image) read out in accordance with an instruction from a control unit 105.

The information processing apparatus 120 processes information that is based on a radiation image in which an object is shot. The information processing apparatus 120 includes the control unit 105, a monitor 106, an operation unit 107, a storage unit 108, an image processing unit 109, and a display control unit 116.

The control unit 105 includes one or more processors (not illustrated), and realizes various types of control of the information processing apparatus 120 as a result of executing programs stored in the storage unit 108. The storage unit 108 stores results of image processing and various programs. The storage unit 108 is constituted by a ROM (Read Only Memory) and a RAM (Random Access Memory), for example. The storage unit 108 can store an image output from the control unit 105, an image subjected to image processing performed by the image processing unit 109, and a calculation result of the image processing unit 109.

The image processing unit 109 processes a radiation image obtained from the FPD 102. For example, according to one mode of the image processing unit 109, at least three types of energy information is obtained from a plurality of radiation images obtained by irradiating an object with radiation. The image processing unit 109 then calculates the thickness or area density of a predetermined substance based on the at least three types of energy information, and calculates an effective atomic number for which the predetermined substance excluded, based on the thickness or area density of the predetermined substance.

The image processing unit 109 processes a radiation image obtained from the FPD 102. The image processing unit 109 includes a substance characteristics calculation unit 110 and an effective atomic number calculation unit 111 as function configurations. These function configurations of the image processing unit 109 will be described later in detail. Note that these function configurations may be realized by a processor of the control unit 105 executing a predetermined program, or may also be realized by using a program read from the storage unit 108 by one or more processors of the image processing unit 109. The processors of the control unit 105 and the image processing unit 109 are each constituted by a CPU (central processing unit), for example. Each of the units of the image processing unit 109 may be constituted by an integrated circuit and the like as long as a similar function is achieved. In addition, a graphic control unit such as a GPU (Graphics Processing Unit), a communication unit such as a network card, an input/output control units such as a keyboard, a display, and a touch panel, and the like can be included as the internal configuration of the information processing apparatus 120.

The monitor 106 (display unit) displays a radiation image (digital image) received from the FPD 102 by the control unit 105 and an image subjected to image processing performed by the image processing unit 109. The display control unit 116 controls display of the monitor 106 (display unit). Instructions to the image processing unit 109 and the FPD 102 can be input using the operation unit 107, and the operation unit 107 accepts input of an instruction to the FPD 102, via a user interface (not illustrated).

In the above-described configuration, the radiation generating apparatus 104 irradiates an object with radiation a plurality of times, and the FPD 102 generates radiation images based on such irradiation. In this embodiment, radiation of three types of energy, namely high energy, intermediate energy, and low energy is emitted from the radiation generating apparatus 104, and the FPD 102 generates a high-energy radiation image $X_H$, an intermediate-energy radiation image $X_M$, and a low-energy radiation image $X_L$. Note that radiation of four or more types of energy may also be emitted, and the number of types of radiation images that are generated may be four or larger. The control unit 105 obtains, from the FPD 102, images that are based on a plurality of types of radiation energy. The control unit 105 obtains the high-energy radiation image $X_H$, the intermediate-energy radiation image $X_M$, and the low-energy radiation image $X_L$, from the FPD 102.

The energy of radiation generated by the radiation tube 101 can be changed as a result of the radiation generating apparatus 104 setting a tube voltage of the radiation tube 101. For example, the radiation tube 101 is set to 120 kV during high-energy irradiation, 100 kV during intermediate-energy irradiation, and 80 kV during low-energy irradiation. The larger the energy difference is, the more preferable it is, but it is favorable to select appropriate energy in consideration of the thickness and exposure amount of the object.

Note that an FPD that can obtain radiation images corresponding to a plurality of types of energy in a single irradiation process may be used as the FPD 102. In this type of FPD 102, sampling is performed a plurality of times for a single process of irradiation from the radiation tube 101. Specifically, the FPD 102 can obtain the high-energy radiation image $X_H$, the intermediate energy radiation image $X_M$, and the low-energy radiation image $X_L$ in a single process of irradiation, by instantaneously performing sampling when starting and ending irradiation of the radiation tube 101. Such a shooting method is effective for preventing a motion artifact from occurring in an object that moves largely such as a heart.

In addition, a configuration may also be adopted in which radiation images of a plurality of types of energy are obtained in a single process of irradiation from the radiation tube 101, using the FPD 102 that has a layered structure with three stages. In this case, in radiation, more beam hardening occurs and the energy is higher at a lower stage. Thus, in a single process of irradiation, the low-energy radiation image $X_L$ can be obtained through output of the first-stage FPD, the intermediate-energy radiation image $X_M$ can be obtained through output of the second-stage FPD, and the high-energy radiation image $X_H$ can be obtained through output of the third-stage FPD. Such a shooting system is effective in that radiation images of a plurality of types of energy are obtained through a single irradiation process without particularly performing control of the radiation tube 101. Also, occurrence of a motion artifact is prevented.

The substance characteristics calculation unit 110 obtains, as $\mu_A(E)$, the linear attenuation coefficient of a predetermined substance (exclusion substance) that is desired to be excluded from calculation of an effective atomic number, and calculates radiation attenuation caused by the exclusion substance, using the thickness $d_A$ of the substance. Note that the mass attenuation coefficient of the exclusion substance may be obtained as $\mu_A(E)$, and the area density of the substance may be used as $d_A$.

The effective atomic number calculation unit 111 calculates the effective atomic number of the remaining substance that remains after excluding the exclusion substance and the area density or thickness of the substance corresponding to that effective atomic number. The effective atomic number calculation unit 111 performs this calculation using a plurality of radiation images that are based on different types of radiation energy and the radiation attenuation of the exclusion substance obtained by the substance characteristics calculation unit 110. Here, the "effective atomic number" refers to an atomic number for a case where elements, compounds, and elements of a compound are considered on the average, and is a quantitative index indicating that radiation is attenuated to the same degree as a substance having the atomic number.

Figure 2:
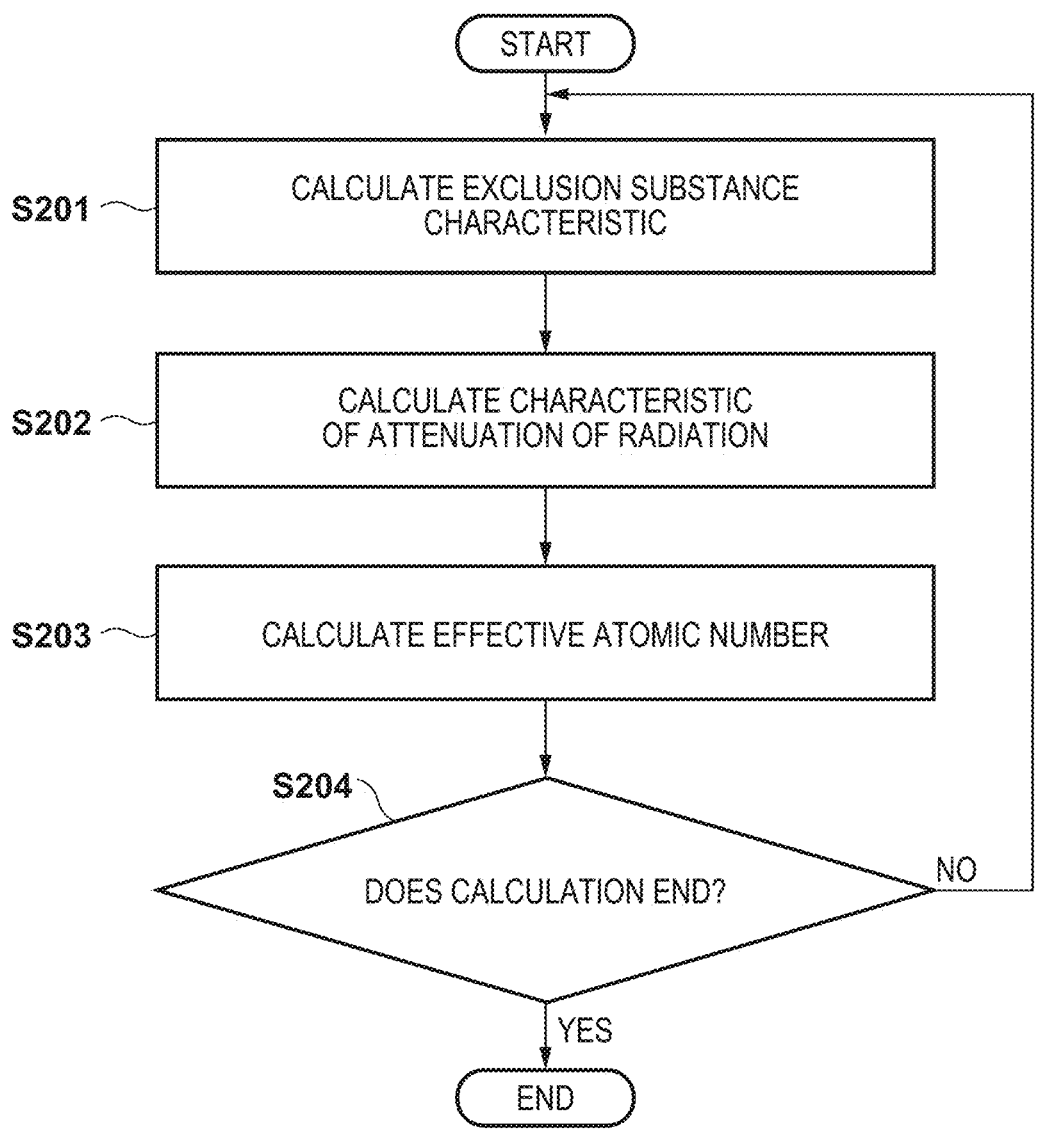
FIG. 2 is a flowchart showing processing that is performed by an image processing unit according to the first embodiment.

Next, processing that is performed by the image processing unit 109 according to the first embodiment will be described in detail with reference to flowchart shown in FIG. 2. The control unit 105 stores, in the storage unit 108, radiation images shot by the FPD 102, and transfers the radiation images to the image processing unit 109. As described above, radiation images corresponding to a plurality of types of energy of radiation are transferred. The image processing unit 109 obtains, for example, at least three radiation images corresponding to at least three types of energy and obtained based on radiation emitted onto an object. The image processing unit 109 executes the following processing using these at least three radiation images obtained from the control unit 105. Note that, in the following description, three radiation images corresponding to three types of radiation energy are used.

In the steps S201 to S203 to be described later, the image processing unit 109 calculates an effective atomic number of a remaining substance that remains after excluding a predetermined substance from the object 103, based on radiation images and characteristics of attenuations of radiation corresponding to at least three types of energy, the characteristics being represented based on the predetermined substance and the remaining substance. In this embodiment, the predetermined substance to be excluded refers to a substance whose effective atomic number is known. First, in step S201, the substance characteristics calculation unit 110 obtains an attenuation coefficient (linear attenuation coefficient or mass attenuation coefficient) of the predetermined substance to be excluded from calculation of an effective atomic number (hereinafter, "exclusion substance"), the attenuation coefficient of the exclusion substance corresponding to the radiation. The substance characteristics calculation unit 110 then calculates radiation attenuation caused by the exclusion substance as expressed in Expression 1 below using the obtained attenuation coefficient.

$$\mu_A(E)d_A \qquad \text{[Expression 1]}$$

Here, $\mu_A$ indicates the linear attenuation coefficient of the exclusion substance, and $d_A$ indicates the thickness of the exclusion substance. Note that the mass attenuation coefficient of the exclusion substance may also be used as $\mu_A$, and the area density of the exclusion substance may also be used as $d_A$. When this processing is performed the first time, a predetermined initial value is used for $d_A$, and, when this processing is performed the second time onward, a calculation result in step S203 to be described later is used. In addition, a configuration may also be adopted in which the user can suitably set the exclusion substance. For example, when it is desired to accurately extract a contrast agent, a stent, and a guide wire, fat that is a thick soft substance may be selected in the abdomen, and bones may be selected in the head and four extremities. Note that the image processing unit 109 may provide a user interface for the user to select an exclusion substance from a plurality of substances that include bones and fat, using the operation unit 107 and the monitor 106, for example.

Next, in step S202, the effective atomic number calculation unit 111 calculates characteristics of attenuations of high-energy radiation, intermediate-energy radiation, and low-energy radiation based on Expressions 2 to 4 below using the attenuation coefficient of the exclusion substance obtained in S201. Expressions 2 to 4 are expressions of characteristics of radiation attenuations corresponding to radiation of three types of energy, the characteristics being represented based on the exclusion substance whose effective atomic number is known and a remaining substance that remains after excluding the exclusion substance from the object 103.

$$I_H = \frac{\int n_H(E)Ee^{-\mu(Z,E)\sigma-\mu_A(E)d_A}dE}{\int n_H(E)EdE} \qquad \text{[Expression 2]}$$

$$I_M = \frac{\int n_M(E)Ee^{-\mu(Z,E)\sigma-\mu_A(E)d_A}dE}{\int n_M(E)EdE} \qquad \text{[Expression 3]}$$

$$I_L = \frac{\int n_L(E)Ee^{-\mu(Z,E)\sigma-\mu_A(E)d_A}dE}{\int n_L(E)EdE} \qquad \text{[Expression 4]}$$

Here, $I_H$ indicates the characteristics of attenuation of high-energy radiation, $I_M$ indicates the characteristics of attenuation of intermediate-energy radiation, and $I_L$ indicates the characteristics of attenuation of low-energy radiation. In addition, $n_H(E)$ indicates the energy spectrum of high-energy radiation emitted onto the object, $n_M(E)$ indicates the energy spectrum of intermediate-energy radiation emitted onto the object, and $n_L(E)$ indicates the energy spectrum of low-energy radiation emitted onto the object. E is a variable indicating energy. In addition, $\mu(Z,E)$ indicates the linear attenuation coefficient of the substance of an effective the atomic number Z (remaining substance that remains after excluding the exclusion substance), and $\sigma$ indicates the thickness of that substance. Alternatively, the mass attenuation coefficient may also be used as $\mu(Z,E)$, and the area density may also be used as $\sigma$.

Note that, when this processing is performed the first time, predetermined initial values are used for Z and $\sigma$, and when this processing is performed the second time and onward, a calculation result obtained in step S203 to be described later is used. In addition, for example, a table available to the public in a database or the like of NIST (National Institute of Standards and Technology) can be used for the attenuation coefficient of the substance of the atomic number Z. Note that, in calculation of an effective atomic number, an atomic number can be a decimal number, and thus a table for interpolating atomic numbers is used.

In step S203, the effective atomic number calculation unit 111 calculates the effective atomic number of the remaining substance that remains after excluding the exclusion substance from the object 103, based on the characteristics of attenuations of radiation corresponding to radiation of the above-described three types of energy and radiation images corresponding to the radiation of the three types of energy. In this embodiment, the effective atomic number calculation unit 111 calculates the effective atomic number Z, the area density $\sigma$ of the substance corresponding to that effective atomic number, and the thickness $d_A$ of the exclusion substance, based on the characteristics $I_H$, $I_M$, and $I_L$ of attenuations of radiation of the respective types of energy calculated in step S202 and the radiation images $X_H$, $X_M$, and $X_L$ of the respective types of energy obtained by shooting an object. In this calculation, three non-linear simultaneous equations need to be solved. Any known technique may be used for the calculation, but, here, the Newton-Raphson method that is a method of successive approximation is used. Specifically, calculation of Expression 5 below is repeated to successively obtain Z, $\sigma$, and $d_A$. Here, k indicates the number of repetitions.

$$\begin{pmatrix} \sigma^{k+1} \\ Z^{k+1} \\ d_A^{k+1} \end{pmatrix} = \begin{pmatrix} \sigma^k \\ Z^k \\ d_A^k \end{pmatrix} - \begin{pmatrix} \frac{\partial I_H^k}{\partial \sigma} & \frac{\partial I_H^k}{\partial Z} & \frac{\partial I_H^k}{\partial d_A} \\ \frac{\partial I_M^k}{\partial \sigma} & \frac{\partial I_M^k}{\partial Z} & \frac{\partial I_M^k}{\partial d_A} \\ \frac{\partial I_L^k}{\partial \sigma} & \frac{\partial I_L^k}{\partial Z} & \frac{\partial I_L^k}{\partial d_A} \end{pmatrix}^{-1} \begin{pmatrix} I_H^k - X_H \\ I_M^k - X_M \\ I_L^k - X_L \end{pmatrix} \quad \text{[Expression 5]}$$

Next, in step S204, the effective atomic number calculation unit 111 determines whether or not to end the calculation. While an end determination criterion is not satisfied (NO in step S204), the above-described processing in step S201 to S203 is repeatedly executed. Note that examples of the determination criterion include the values of Z, $\sigma$, and $d_A$ calculated in step S203 having reached a predetermined accuracy, the update amount of a value due to iterative calculation having decreased sufficiently, and the number of repetitions having reached a predetermined number of times.

As a result of performing the above processing on all of the pixels of the radiation images $X_H$, $X_M$, and $X_L$ of the respective types of energy, Z, $\sigma$, and $d_A$ of each of the pixels are obtained. The image processing unit 109 can use these to generate an effective atomic number image, and a thickness image (or an area density image) of a substance corresponding to the effective atomic number. That is to say, the image processing unit 109 has a function of a generation unit that generates image data obtained through imaging of the effective atomic number obtained for the remaining substance that is other than the exclusion substance. In other words, the image processing unit 109 can calculate the effective atomic number of the remaining substance, excluding the exclusion substance. The image data can be displayed on the monitor 106 by the display control unit 116. In addition, the image processing unit 109 may also include an extraction unit that extracts a contrast agent, a medical device, or a lesion based on image data. As will be described later regarding an effective atomic number image 3b in FIG. 3, as a result of using the effective atomic number image for which the exclusion substance is excluded, the contrast agent and the like can be more accurately and easily extracted. Note that the effective atomic number Z and $\sigma$ obtained by performing the above processing respectively indicate the effective atomic number of the substance from which the exclusion substance is excluded and the thickness/area density thereof. Note that, if the density of the substance is known, as a result of multiplying the area density by the density, conversion can be made into a thickness, and the area density and the thickness take values such that they can be mutually converted into each other.

Figure 3:
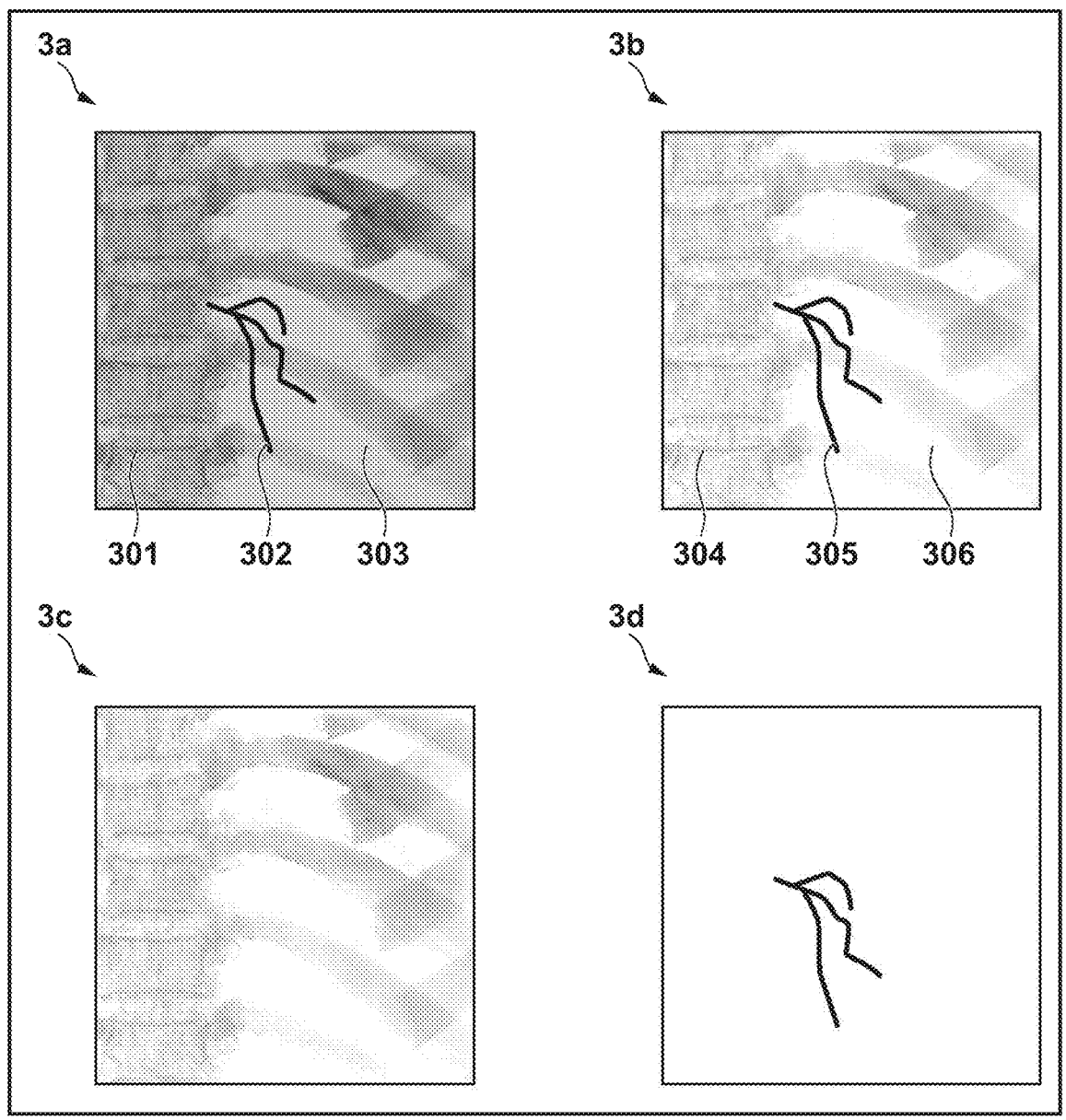
FIG. 3 is a diagram illustrating an image obtained through imaging of an effective atomic number.

Next, the characteristics (effects) of images generated according to this embodiment will be described with reference to FIG. 3. In FIG. 3, reference numeral 3a denotes a schematic diagram of an effective atomic number image that is generated through general processing that uses radiation images of two types of energy. Reference numeral 3b denotes a schematic diagram of an effective atomic number image that uses radiation images of three types of energy according to this embodiment. Here, reference numerals 301 and 304 denote bones, reference numerals 302 and 305 denote a contrast agent, and reference numerals 303 and 306 denote soft tissue.

The effective atomic number image 3a in FIG. 3 is calculated by repeating Expressions 6 to 8 below.

$$I_H = \frac{\int n_H(E) E e^{-\mu_A(E) d_A} dE}{\int n_H(E) E dE} \quad \text{[Expression 6]}$$

$$I_L = \frac{\int n_L(E) E e^{-\mu_A(E) d_A} dE}{\int n_L(E) E dE} \quad \text{[Expression 7]}$$

$$\begin{pmatrix} \sigma^{k+1} \\ Z^{k+1} \end{pmatrix} = \begin{pmatrix} \sigma^k \\ Z^k \end{pmatrix} - \begin{pmatrix} \frac{\partial I_H^k}{\partial \sigma} & \frac{\partial I_H^k}{\partial Z} \\ \frac{\partial I_L^k}{\partial \sigma} & \frac{\partial I_L^k}{\partial Z} \end{pmatrix}^{-1} \begin{pmatrix} I_H^k - X_H \\ I_L^k - X_L \end{pmatrix} \quad \text{[Expression 8]}$$

Simulation is performed using iodine as a contrast agent, and thus the atomic number of the contrast agent is 53, but, in the effective atomic number image 3a, the value of the effective atomic number of the contrast agent 302 is approximately 7. This is because the soft tissue 303 of the human body is very thick compared with the contrast agent 302, and thus the effective atomic number has been subjected to averaging. Similarly, the effective atomic number of bones is 12.3 to 13.8, but, in the effective atomic number image 3a, the value of the effective atomic number of the bone 301 is approximately 6.7.

On the other hand, the value of approximately 53, which is an intrinsic value, is obtained as the effective atomic number of the contrast agent 305 in the effective atomic number image 3b in FIG. 3. This is because soft tissue (fat) is excluded from calculation of an effective atomic number expressed as Expressions 2 to 5. Similarly, also in the effective atomic number image 3b, the value of the effective atomic number of the bone 304 is approximately 12, which is an intrinsic value of the effective atomic number.

Furthermore, as a result of extracting the contrast agent through threshold value processing or the like, it is also easy to extract, from the effective atomic number image 3b, an image 3c of only bones and an image 3d of only angiographic blood vessels, which are shown in FIG. 3. On the other hand, in the effective atomic number image 3a in FIG. 3, the effective atomic numbers of the bone, soft substances, and contrast agent are close, and it is more difficult to separate the image of bones and the image of angiographic blood vessels from each other.

As described above, according to the first embodiment, as a result of excluding a predetermined substance as an exclusion substance, it is possible to accurately calculate the effective atomic number of a substance other than the exclusion substance. For example, as a result of excluding soft tissue as an exclusion substance, it is possible to accurately calculate the effective atomic numbers of a contrast agent and bones, which are substances other than the exclusion substance. Accordingly, it is possible to accurately render a stenosed vessel and the like, and medical practitioners are enabled to easily and accurately perform diagnosis and treatment. Therefore, it is possible to achieve a reduction in the contrast agent amount and a prompt surgical technique, and realize an efficient and less invasive medical technique.

Note that it is easy to perform detection of not only a contrast agent but also detection of a medical device such as a stent, a catheter, or a coil, and identification of a lesion that includes detection a urinary acid for diagnosis of gout. Furthermore, in the first embodiment, an example has been described in which three substances, namely bones, soft tissue, and a contrast agent are included, but, even if there are four or more substances that include medical device or the like, substances can be easily identified.

Second Embodiment

In a second embodiment, an iterative calculation such as the Newton-Raphson method is used for calculation of an effective atomic number of a remaining substance that remains after excluding a predetermined substance. In the second embodiment, as a result of approximating each of a plurality of types of energy to monochromatic energy, the effective atomic number of the remaining substance that remains after excluding the predetermined substance is obtained in a simple manner without using iterative calculation. Note that the configuration of the radiography system 100 according to the second embodiment is similar to the first embodiment (FIG. 1).

Processing that is performed by the image processing unit 109 according to the second embodiment will be described in detail with reference to the flowchart in FIG. 4. The control unit 105 stores, in the storage unit 108, radiation images shot by the FPD 102, and transfer the radiation images to the image processing unit 109.

In step S401, the substance characteristics calculation unit 110 obtains attenuation coefficients (linear attenuation coefficients or mass attenuation coefficients) of an exclusion substance. More specifically, the substance characteristics calculation unit 110 obtains attenuation coefficients ($\mu_A(E_H)$, $\mu_A(E_M)$, and $\mu_A(E_L)$) of the exclusion substance respectively at $E_H$, $E_M$, and $E_L$ obtained by approximating $n_H(E)$, $n_M(E)$, and $n_L(E)$ to monochromatic energy. Approximation to monochromatic energy will be described in detail in step S402.

In step S402, the effective atomic number calculation unit 111 calculates characteristics of attenuations of high-energy radiation, intermediate-energy radiation, and low-energy radiation, using the attenuation coefficients of the exclusion substance calculated in step S401. According to the second embodiment, the energy spectra $n_H(E)$, $n_M(E)$, and $n_L(E)$ of radiation in Expressions 2 to 4 of the first embodiment are approximated to monochromatic energy, namely using delta functions $\delta(E_H)$, $\delta(E_M)$, and $\delta(E_L)$. Here, $E_H$, $E_M$, and $E_L$ each indicates a representative value of an energy spectrum, and, for example, can take the average energy or the peak position of the spectrum. Accordingly, Expressions 2 to 4 of the first embodiment respectively replaced with Expressions 9 to 11 below.

$$I_H = e^{-\mu(Z,E_H)\sigma - \mu_A(E_H)d_A} \quad \text{[Expression 9]}$$

$$I_M = e^{-\mu(Z,E_M)\sigma - \mu_A(E_M)d_A} \quad \text{[Expression 10]}$$

$$I_L = e^{-\mu(Z,E_L)\sigma - \mu_A(E_L)d_A} \quad \text{[Expression 11]}$$

Furthermore, as a result of performing logarithmic conversion on Expressions 9 to 11, Expressions 12 to 14 are obtained.

$$-\ln I_H = \mu(Z,E_H)\sigma + \mu_A(E_H)d_A \quad \text{[Expression 12]}$$

$$-\ln I_M = \mu(Z,E_M)\sigma + \mu_A(E_M)d_A \quad \text{[Expression 13]}$$

$$-\ln I_L = \mu(Z,E_L)\sigma + \mu_A(E_L)d_A \quad \text{[Expression 14]}$$

Next, Next, in step S403, the effective atomic number calculation unit 111 calculates the effective atomic number Z and the area density $\sigma$ of the substance from which the exclusion substance is excluded and the thickness of $d_A$ of the exclusion substance, using Expressions 12 to 14. Specifically, if Expressions 12 to 14 are simplified and $\sigma$ and $d_A$ are erased, Expression 15 below is obtained. In Expression 15, an only unknown variable is Z, and thus, it is possible to obtain the effective atomic number Z by solving Expression 15 using a known method such as a bisection method.

$$\frac{\mu(Z,E_H)\ln I_M - \mu(Z,E_M)\ln I_H}{\mu_A(E_H)\mu(Z,E_M) - \mu_A(E_M)\mu(Z,E_H)} = \quad \text{[Expression 15]}$$

$$\frac{\mu(Z,E_H)\ln I_L - \mu(Z,E_L)\ln I_H}{\mu_A(E_H)\mu(Z,E_L) - \mu_A(E_L)\mu(Z,E_H)}$$

In addition, the effective atomic number calculation unit 111 calculates $\sigma$ and $d_A$ based on Expression 16 below, using the result of Expression 15.

$$\begin{pmatrix} \sigma \\ d_A \end{pmatrix} = \begin{pmatrix} \mu(Z,E_H) & \mu_A(E_H) \\ \mu(Z,E_L) & \mu_A(E_L) \end{pmatrix}^{-1} \begin{pmatrix} -\ln I_H \\ -\ln I_L \end{pmatrix} \quad \text{[Expression 16]}$$

As described above, according to the second embodiment, numerical integration of Expressions 2 to 4 and iterative calculation of Expression 5 according to the first embodiment are unnecessary, and thus it is possible to calculate the effective atomic number, for which the exclusion substance (for example, soft tissue) is excluded, at a higher speed than in the first embodiment. As a result, the image processing unit 109 can generate a moving image, in imaging of the effective atomic number of the remaining substance that remains after excluding the exclusion substance. Accordingly, according to the second embodiment, a stenosed vessel and the like can be accurately rendered even in a moving image of radiation (fluorography) particularly. Therefore, medical practitioners are enabled to easily and accurately perform diagnosis and treatment, and it is possible to achieve a reduction in the contrast agent amount and a prompt surgical technique, and realize a convenient and less invasive medical technique.

As described above, according to the embodiments, as a result of calculating the effective atomic number of the remaining substance that remains after excluding the exclusion substance whose effective atomic number is known (specifically, attenuation coefficient is known), a more accurate effective atomic number that is not affected by the exclusion substance (for example, fat) is obtained. Therefore, according to the embodiments, even when radiation passing through an object has passed through two or more types of substances, it is possible to accurately calculate the effective atomic number without energy information being averaged, as a result of excluding a specific substance from a radiation image as an exclusion substance.

According to the present invention, it is possible to more accurately calculate an effective atomic number in a radiation image.

OTHER EMBODIMENTS

The present invention is not limited to the above embodiments, and can be carried out as appropriate with changes within the spirit of the invention. The present invention can also adopt an embodiment as a system, an apparatus, a method, a program, a storage medium or the like. Specifically, the present invention may be applied to a system constituted by a plurality of devices, or an apparatus constituted by one device.

Other Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An information processing apparatus, comprising:
at least one of (a) one or more processors connected to one or more memories storing a program including instructions executed by the one or more processors and (b) circuitry configured to perform:
obtaining at least three radiation images obtained based on radiation emitted onto an object, each of the at least three radiation images corresponding to each of at least three types of energy; and
calculating, by separating a predetermined substance having a known attenuation coefficient in the object and a remaining substance other than the predetermined substance in the object based on the at least three radiation images, an effective atomic number of the remaining substance.

2. The information processing apparatus according to claim 1, wherein in the calculating, a thickness or an area density of the predetermined substance, the effective atomic number of the remaining substance, and a thickness or an area density of the remaining substance are calculated using a known attenuation coefficient of the predetermined substance.

3. The information processing apparatus according to claim 1, wherein in the calculating, a thickness or an area density of the predetermined substance, a thickness or an area density of the remaining substance, and the effective atomic number of the remaining substance are calculated by solving a non-linear simultaneous equation obtained based on the at least three radiation images and equations expressing attenuations of radiation caused by the predetermined substance and the remaining substance corresponding to the at least three types of energy.

4. The information processing apparatus according to claim 3, wherein the non-linear simultaneous equation is solved through a successive approximation.

5. The information processing apparatus according to claim 3, wherein the non-linear simultaneous equation is solved with approximating each of the at least three types of energy to monochromatic energy.

6. The information processing apparatus according to claim 1, wherein the predetermined substance is a bone or fat.

7. The information processing apparatus according to claim 1, wherein the at least one of (a) one or more processors and (b) circuitry is configured to further perform providing a user interface for a user to select the predetermined substance from a plurality of substances that include a bone and fat.

8. The information processing apparatus according to claim 1, wherein the at least one of (a) one or more processors and (b) circuitry is configured to further perform generating image data representing the remaining substance based on the effective atomic number of the remaining substance.

9. The information processing apparatus according to claim 8, wherein the at least one of (a) one or more processors and (b) circuitry is configured to further perform displaying the image data on a display.

10. The information processing apparatus according to claim 8, wherein the image data is a moving image.

11. The information processing apparatus according to claim 8, wherein the at least one of (a) one or more processors and (b) circuitry is configured to further perform extracting a contrast agent, a medical device, or a lesion based on the image data.

12. A radiography system, comprising:
a radiation detector configured to obtain a radiation image based on radiation emitted onto an object;
an information processing apparatus comprising at least one of (a) one or more processors connected to one or more memories storing a program including instructions executed by the one or more processors and (b) circuitry configured to perform:
obtaining at least three radiation images from the radiation detector, each of the at least three radiation images corresponding to each of at least three types of energy; and
calculating, by separating a predetermined substance having a known attenuation coefficient in the object and a remaining substance other than the predetermined substance in the object based on the at least three radiation images, an effective atomic number of the remaining substance.

13. A radiography system, comprising:
a radiation detector configured to obtain a radiation image based on radiation emitted onto an object; and
an information processing apparatus configured to:
obtain at least three types of energy information from a plurality of radiation images obtained from the radiation detector;
calculate a thickness or an area density of a predetermined substance, based on the at least three types of energy information; and
calculate an effective atomic number for which the predetermined substance is excluded, based on the thickness or the area density of the predetermined substance.

14. An information processing method, comprising:
obtaining at least three radiation images based on radiation emitted onto an object, each of the at least three radiation images corresponding to each of at least three types of energy; and
calculating, by separating a predetermined substance having a known attenuation coefficient in the object and a remaining substance other than the predetermined substance in the object based on the at least three radiation images, an effective atomic number of the remaining substance.

15. A non-transitory computer-readable storage medium storing a program for causing a computer to execute an information processing method, comprising:
obtaining at least three radiation images obtained based on radiation emitted onto an object, each of the at least three radiation images corresponding to each of at least three types of energy; and
calculating, by separating a predetermined substance having a known attenuation coefficient in the object and a remaining substance other than the predetermined substance in the object based on the at least three radiation images, an effective atomic number of the remaining substance.

* * * * *